United States Patent
Okada et al.

(10) Patent No.: US 12,038,440 B2
(45) Date of Patent: Jul. 16, 2024

(54) LECTIN-BINDING SUBSTANCE MEASUREMENT METHOD, LECTIN-BINDING SUBSTANCE MEASUREMENT KIT, AND CAPTURE CARRIER FOR USE IN THESE

(71) Applicant: FUJIREBIO INC., Tokyo (JP)

(72) Inventors: Kazunori Okada, Hachioji (JP); Kumiko Iida, Hachioji (JP); Shintaro Yagi, Hachioji (JP); Katsumi Aoyagi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 0 days.

(21) Appl. No.: 17/639,400

(22) PCT Filed: Sep. 1, 2020

(86) PCT No.: PCT/JP2020/033141
§ 371 (c)(1),
(2) Date: Mar. 1, 2022

(87) PCT Pub. No.: WO2021/045065
PCT Pub. Date: Mar. 11, 2021

(65) Prior Publication Data
US 2022/0326246 A1    Oct. 13, 2022

(30) Foreign Application Priority Data
Sep. 2, 2019   (JP) .................. 2019-159748

(51) Int. Cl.
*G01N 33/574* (2006.01)
(52) U.S. Cl.
CPC .............. *G01N 33/57484* (2013.01); *G01N 2333/471* (2013.01)
(58) Field of Classification Search
CPC .............................................. G01N 33/57484
See application file for complete search history.

(56) References Cited

U.S. PATENT DOCUMENTS

| | | | |
|---|---|---|---|
| 4,692,330 A | 9/1987 | Ryohei et al. | |
| 9,874,558 B2 | 1/2018 | Isoda et al. | |
| 2008/0153089 A1 | 6/2008 | Aoyagi | |
| 2013/0052653 A1 | 2/2013 | Stein et al. | |
| 2013/0230897 A1 | 9/2013 | Ohiro et al. | |
| 2016/0313315 A1 | 10/2016 | Tran et al. | |
| 2017/0059562 A1 | 3/2017 | Kawamoto et al. | |

FOREIGN PATENT DOCUMENTS

| | | | |
|---|---|---|---|
| JP | S61-79164 A | | 4/1986 |
| JP | H07-083922 A | | 3/1995 |
| JP | H07-325083 A | | 12/1995 |
| JP | 5076878 B2 | * | 11/2012 |
| JP | 2016-539339 A | | 12/2016 |
| JP | 2017-049059 A | | 3/2017 |
| JP | 2018-004323 A | | 1/2018 |
| WO | 2006/070732 A1 | | 7/2006 |
| WO | 2011/066449 A1 | | 6/2011 |
| WO | 2011/129357 A1 | | 10/2011 |
| WO | 2013/021962 A1 | | 2/2013 |
| WO | 2017/011876 A1 | | 1/2017 |
| WO | 2017/183711 A1 | | 10/2017 |

OTHER PUBLICATIONS

Kimikazu et al., JPH07325083A translated Description, 1995, Espacenet (Year: 1995).*
Mar. 8, 2022 International Preliminary Report on Patentability issued in International Patent Application No. PCT/JP2020/033141.
Dec. 1, 2020 International Search Report issued in International Patent Application No. PCT/JP2020/033141.
Aug. 29, 2023 Extended European Search Report issued in European Patent Application No. 20859955.5.

* cited by examiner

*Primary Examiner* — Paul S Hyun
*Assistant Examiner* — Mickey Huang
(74) *Attorney, Agent, or Firm* — Oliff PLC

(57) ABSTRACT

A lectin-binding substance measurement method is a method for measuring a lectin-binding substance in a sample, and includes: a capturing step of bringing a capture carrier including a water-insoluble carrier and a molecule immobilized on the water-insoluble carrier, the molecule being a molecule capable of capturing a lectin-binding substance, into contact with the sample to cause the capture carrier to capture the lectin-binding substance; a washing step of removing contaminants unbound to the capture carrier; a releasing step of releasing the lectin-binding substance from the capture carrier to obtain a prepared sample; and a measuring step of measuring the lectin-binding substance in the prepared sample by using a lectin.

4 Claims, No Drawings

LECTIN-BINDING SUBSTANCE MEASUREMENT METHOD, LECTIN-BINDING SUBSTANCE MEASUREMENT KIT, AND CAPTURE CARRIER FOR USE IN THESE

TECHNICAL FIELD

The present invention relates to a lectin-binding substance measurement method, a lectin-binding substance measurement kit, and a capture carrier for use in these.

BACKGROUND ART

In recent years, as markers for monitoring malignant diseases such as tumor markers, methods for measuring glycans or substances having glycans such as glycoproteins, glycolipids, and free glycans have been actively studied. Among these, a measurement method using a lectin that binds to a glycan portion of a measurement target substance and a measurement method using a combination of the above measurement method and measurement using an antibody of the measurement target substance have been attracting attention from the viewpoint of the ability to measure not only a quantitative change in a measurement target substance but also a qualitative change due to a change in a glycan therein. As such a measurement target substance (lectin-binding substance) that can be measured by using a lectin, for example, α-fetoprotein L3 (AFP-L3) having a glycan to which fucose is added (core fucose structure) is known to be a marker highly specific to hepatocellular carcinoma among ay-fetoproteins (AFP), which are carcinoembryonic glycoproteins expressed in hepatitis, hepatic cirrhosis, hepatocellular carcinoma, and so on. Currently, "μTASWako AFP-L3", which is a combination of an antibody that binds to an AFP portion and a lectin (*lens culinaris* agglutinin (LCA)) that binds to a core fucose structure, is manufactured and sold as a reagent for detecting an AFP-L3 fraction by FUJIFILM Wako Pure Chemical Corporation. For this reagent, the LBA method (Liquid-phase Binding Assay) is used in which an immune complex formed after an antigen-antibody reaction is separated and measured in a liquid phase by an ion exchange column or electrophoresis. However, it is necessary to use a dedicated machine or the like with low versatility designed for carrying out the above method, and therefore there is a problem that the measurement cost is high.

As another method for measuring the above lectin-binding substance, for example, International Publication No. WO2017/183711 (PTL 1) describes a method for capturing lectin-target molecules (le tin-binding substance), the method including binding lectin to the lectin-target molecules in the presence of a lectin-reactive glycan-containing entity.

In addition, in immunological measurement methods using a complex composed of a probe such as an antibody and a labeling substance such as an enzyme, various studies have been conducted for the purpose of enhancing the sensitivity and speeding up. For example, International Application Japanese-Phase Publication No. 2016-539339 (PLT 2) describes a method for determining the quantity of an analyte in a sample, the method including performing a purification step before quantification of the analyte by immunoassay or the like, the purification step including a step of: mixing the sample, a dilapidation agent, and first magnetic particles coated with first analyte binding partners; binding the analyte contained in the sample to the first analyte binding partners; thereafter removing unbound reagents; and releasing the analyte.

CITATION LIST

Patent Literature

[PTL 1] International Publication No. WO2017/183711
[PTL 2] International Application Japanese-Phase Publication No. 2016-539339

SUMMARY OF INVENTION

Technical Problem

However, a simple method for measuring a lectin-binding substance using a lectin has not yet been fully studied. In addition, the method for measuring a lectin-binding substance by using a lectin has a problem that, in the case where, for example, serum is used as a sample containing the lectin-binding substance, measurement with high specificity is difficult because the lectin non-specifically hinds to a substance other than the target substance (for example, a lectin-recognizing glycan bound to a protein other than the target) and thereby generates high background. Moreover, in the immunological measurement methods, there is generally conducted a method for reducing interference of contaminants by diluting the sample, but this method has a problem of being difficult to apply to a measurement method using a lectin because the lectin has weak affinity for glycans as compared with antigen-antibody reaction.

The present invention has been made in consideration of the above problems, and has an object to provide a lectin-binding substance measurement method and a lectin-binding substance measurement kit, which are capable of measuring a lectin-binding substance in a sample with high sensitivity in a simple procedure, and provide a capture carrier for use in these.

Solution to Problem

The present inventors have completed the present invention by finding out that, in a method for measuring a lectin-binding substance in a sample by using a lectin, a specific purification treatment before the measurement using the lectin makes it possible to improve the measurement sensitivity of the lectin-binding substance sufficiently reducing the influence of the background even in the case of using a sample such as serum, the purification treatment including: bringing a capture carrier including water-soluble carrier and a molecule immobilized on the water-insoluble carrier, the molecule being capable of capturing the lectin-binding substance, into contact with the sample to cause the capture carrier to capture the lectin-binding substance; removing contaminants unbound to the capture carrier; then re-releasing the lectin-binding substance from the capture carrier; and using this lectin-binding substance in the measurement.

The aspects of the present invention obtained from such findings are as follows.

(1) A lectin-binding substance measurement method for measuring a lectin-binding substance in a sample, including:
  a capturing step of bringing a capture carrier including a water-insoluble carrier and a molecule immobilized on the water-insoluble carrier, the molecule being a molecule capable of capturing a lectin-binding substance, into contact with the sample to cause the capture carrier to capture the lectin-binding substance;

washing step of removing contaminants unbound to the capture carrier;

a releasing step of releasing the lectin-binding substance from the capture carrier to obtain a prepared sample; and a measuring step of measuring the lectin-binding substance in the prepared sample by using a lectin.

(2) The lectin-binding substance measurement method according to (1), in which the measuring step includes a step of bringing a labeled lectin including a labeling substance and a lectin into contact with the prepared sample.

(3) The lectin-binding substance measurement method according to (1) or (2), in which the measuring step includes a step of bringing a blocked labeled lectin including a water-soluble carrier made of a first water-soluble polymer and a labeling substance and a lectin immobilized on the water-soluble carrier into contact with the prepared sample.

(4) The lectin-binding substance measurement method according to any one of (1) to (3), in which the measuring step is carried out in the presence of a second water-soluble polymer.

(5) A capture carrier for use in the lectin-binding substance measurement method according to any one of (1) to (4), including a water-insoluble carrier and a molecule immobilized on the water-insoluble carrier, in which the molecule is a molecule capable of capturing the lectin-binding substance.

(6) A lectin-binding substance measurement kit for measuring a lectin-binding substance in a sample, including the capture carrier according to (5).

(7) The lectin-binding substance measurement kit according to (6), further including a labeled lectin including a labeling substance and a lectin.

(8) The lectin-binding substance measurement kit according to (6) or (7), further including a blocked labeled lectin including a water-soluble carrier made of a first water-soluble polymer and a labeling substance and a lectin immobilized on the water-soluble carrier.

(9) The lectin-binding substance measurement kit according to any one of (6) to further including a second water-soluble polymer.

Although the reason why the above object is achieved by the configuration of the present invention not exactly clear, the present inventors presume as follows. Specificity, when the method for measuring a lectin-binding substance by using a lectin is applied to a sample, such as serum, containing many contaminants (for example, a lectin recognizing glycan bound to a protein or the like other than a target) other than a target substance (for example, a glycoprotein), the lectin non-specifically binds to these contaminants and generates high background. In contrast, in the lectin-binding substance measurement of the present invention, the present inventors presume that a purification treatment using a capture carrier in which molecules capable of capturing the lectin-binding substance are immobilized on a water-insoluble carrier drastically reduces the concentration of the contaminants and thereby enables obtaining of a sample containing the target lectin-binding substance at a high concentration, so that the lectin-binding substance can be measured with high sensitivity.

In addition, it was difficult to measure qualitative change in the glycans in a target lectin-binding substance only by conventional immunological measurement using an antibody. According to the present invention, however, a combination of purification using such molecules capable of capturing a lectin-binding substance and measurement using a lectin makes it possible to measure the lectin-binding substance with higher accuracy. Furthermore, the above purification treatment can be performed in a short time, and the purification treatment can change the liquid property of a sample to a buffer level, so that the lectin-binding substance can be easily measured.

Advantageous Effects of Invention

According to the present invention, it is possible to provide a lectin-binding substance measurement method and a lectin-binding substance measurement kit, which are capable of measuring a lectin-binding substance in a sample with high sensitivity in a simple procedure, and provide a capture carrier for use in these.

DESCRIPTION OF EMBODIMENTS

Hereinafter, the present invention will be described in detail according to preferred embodiments thereof.

A lectin-binding substance measurement method is a method for measuring a lectin-binding substance in a sample, the method including a capturing step of bringing a capture carrier including a water-insoluble carrier and a molecule immobilized on the water-insoluble carrier, the molecule being a molecule capable of capturing the lectin-binding substance, into contact with the sample to cause the capture carrier to capture the lectin-binding substance; a washing step of removing contaminants unbound to the capture carrier; a releasing step of releasing the lectin-binding substance from the capture carrier to obtain a prepared sample; and a measuring step of measuring the lectin-binding substance in the prepared sample by using a lectin. In addition, a lectin-binding substance measurement kit of the present invention is a kit for measuring a lectin-binding substance in a sample, the kit including the capture carrier. Further, a capture carrier of the present invention is the aforementioned capture carrier for use in the lectin-binding substance measurement method and the lectin-binding substance measurement kit of the present invention described above.

[Sample]

A sample for use in the lectin-binding substance measurement method of the present invention is not particularly limited as long as it is a sample in which a lectin-binding substance can exist. In general, there are samples collected from a subject (preferably human), such as a diagnostic subject, for which a target lectin-binding substance is to be measured, the samples including: blood samples such as serum, plasma, and whole blood; urine; stool; oral mucosa; pharyngeal mucosa; intestinal mucosa; various kinds of biopsy samples; and so on. A preferable sample according to the present invention is an aqueous sample, and is serum or plasma. These samples may be diluted on an as-needed basis.

[Lectin-Binding Substance]

In the present invention, a "lectin-binding substance" refers to a glycan capable of binding to a lectin (a glycan having a lectin-binding glycan structure) or a substance having the glycan. More specifically, such lectin-binding substances include glycoproteins having a glycan capable of binding to a lectin, glycolipids having the glycan, and carbohydrates containing the glycan.

The lectin is a protein that recognizes a specific glycan structure and exhibits binding activity. As lectins, there are known, for example, lectins derived from animals (for example, vertebrates and invertebrates), plants (for example, leguminosae and poaceae), fungi (for example, mushrooms and rice malt).

The lectins can be classified into fucose-specific lectins having an affinity for fucose, galectins having an affinity for galactose, sialic acid-reactive lectins, and so on depending on a glycan structure for which a lectin has an affinity. More specific examples of the lectins include *Anguilla anguilla* agglutinin (AAA), *Aleuria aurantia* lectin (AAL), *Agaricus blazei* lectin (ABL), *Agrocybe cylindracea* galectin (ACG), *Amaranthus caudatus* lectin (ACL), *Aspergillus oryzae* lectin (AOL), *Arum maculatum* lectin (AML), *ALLIUM sativum* lectin (ASL), banana lectin (BanLec), *Burkholderia cepacian* lectin (BC2L), *Bauhinia purpurea* lectin (BPL), *Colchicum autumnale* lectin (CA), *Caragana arborescens* agglutinin (CAA), *Calysteaia sepium* lectin (Calsepa), *Coprinopsis cinerea* lectin (CGL2), *Cicer arietinum* agglutinin (CPA), *Cytisus sscoparius* lectin (CSA), *Canavalia ensiformis* lectin (Concanavalin A, ConA), *Dolichol biflorus* agglutinin (DBA), *Dictyostelium discoideum* lectin (Discoidin I), *Dictyostelium discoideum* lectin (Discoidin II), *Datura stramonium* lectin (DSL), *Sambucus nigra* agglutinin (SNA), *Erythrina cristagalli* lectin (ECL), *Euonymus europaeus* lectin (EEL), *Escherichia coli*-derived cilia adhering substance F17G variant a (*Escherichia coli* lectin, F17AG), *Galanthus nivalis* lectin (GNL), *Griffonia simplicufolia* lectin I, GSL I), *Griffonia simplicufolia* lectin II (GSL II), *Homarus americanus* lectin (HMA), *Helix pomatia* agglutinin (HPA), *Hippeastrum* hybrid lectin (HHL), *Iris* hybrid, IRA), jack fruit lectin (Jacalin), *Laburnum anagyroides* lectin (LAL), Lima bean agglutinin (LEA), *Lens culinaris* agglutinin (LCA), *Lotus tetragonolobus* lectin (LTL), *Lycopersicon esculentum* lectin (LEL), *Maackia amurensis* leukoagglutinin lectin (*Maackia amurensis* lectin I, MAM), *Maackia amurensis* agglutinin lectin (*Maackia amurensis* lectin II, MAA), *Marasmius oreades* agglutinin (MOA), *Maclura pornifera* lectin. (MPL), *Narcissus pseudonarcissus* lectin (NPL), *Oryza sativa* lectin (Orysata), *Pseudomonas aeruginosa* lectin I (PA-IL), *Pseudomonas aeruginosa* lectin II (PA-TIL), *Phlebodium aureum* lectin (PAL), *Phaseolus vulgaris* aggiutinin-E, -L, -P (PHA-E, -L, -P), peanut agglutinin (PNA), *Pholiota squarrosa* lectin (PhoSL), *Pleurocybella porrigens* lectin (PPL), *Pisum sativum* agglutinin (PSA), *Polyporus squamosus* lectin 1a (PSL 1a), *Psophocarpus tetragonolobus* lectin I (PTL I), *Psophocarpus tetragonolobus* lectin II (PTL II), pokeweed mitogen (PWM), *Ricinus communis* agglutinin I (RCA I), *Ricinus communis* agglutinin II (RCA II), *Robinia pseudoacacia* agglutinin (RPA), *Ralstonia solanacearum*-Fuc lectin (RS-Fuc), *Sambucus sieboldiana* agglutinin (SAME), soybean agglutinin (SBA), *Salvia horminum* agglutinin (SHA), *Sophora japonica* agglutinin (SJA), *Salvia sclarea* agglutinin (SSA), *Solanum tuberosum* lectin (STL), tulip lectin (TL), *Urtica dioica* agglutinin (UDA), *Ulex europaeus* agglutinin I (UEA I), *Ulex europaeus* agglutinin II (UEA II), *Vigna radiata* agglutinin (VRA), *Vicia villosa* lectin (VVL), *Wisteria floribunda* agglutinin (WFA), wheat germ agglutinin (WGA), and so on.

The lectin-binding substance according to the present invention is not particularly limited, but is preferably a glycoprotein or glycolipid for use as a marker for monitoring a malignant disease such as a tumor marker, and more preferably a glycoprotein having a glycan capable of binding to the lectin. As the glycoprotein, there are glycoproteins derived from mammalian, birds, reptiles, amphibians, fishes, plants, insects, microbes, or viruses. More specifically, examples of the glycoprotein include α-fetoprotein (such as AFP-L3), basic fetoprotein (BFP), CA125, CA15-3, CA19-9, CA242, CA50, CA72.4, SPan-1, DUPAN-2, carcinoembryonic antigen (CEA), c-erB-2, cytokeratin 19 fragment (CYFRA), KL-6, elastase I, topcoat antigen, ganglioside fucosylated GM1 (Fuc-GM1), kallikrein-8, matriptase, immunity suppressive acidic protein, nerve cell adhesion factor (NCAM), NCC-ST-439, nerve-specific enolase (NSE), prostatic acidic phosphatase (PAP), protein induced by vitamin K absence or antagonist II (PIVKA-II), tissue polypeptide antigen, squamous cell carcinoma-related antigen (SCC), prostate-specific antigen (PSA), sialyl Lex-i antigen (SLX), sialyl Tn antigen (STN), tissue polypeptide antigen (TPA), γGTP, various immunoglobulins, facto-series carbohydrate antigen, ganglioside, transferrin, haptoglobin, hemopexin, thyroglobulin, human chorionic gonadotropin (hCG), carcinoembryonic antigen-related cell adhesion molecule 1 (CEACAM1), cytoskeleton associated protein 4 (CKAP4), virus particles and virus-derived proteins, glypican, cadoherin, integrin, various membrane proteins, various extracellular matrix constituent proteins, various enzymes, and various carbohydrate antigens. The glycoprotein may be one kind of these alone or include two or more kinds of these. From the viewpoint of being more suitable for a method for assisting diagnosis specific to a malignant disease, the lectin-binding substance according to the present invention is preferably at least one kind selected from the group consisting of glycoproteins having a glycan capable of binding to a fucose-specific lectin among the above glycoproteins, is more preferably at least one kind selected from the group consisting of AFP-L3 and PSA (prostate-specific antigen), and is further preferably any one kind of these. Here, it is preferable to exclude antibodies each of which specifically recognizes a lectin from the lectin-ding substance according to the present invention.

[Capture Carrier (Target Substance-Capture Molecule-Immobilized Carrier)]

In the present invention, a "capture carrier" is a complex including a water-insoluble carrier and a molecule immobilized on the water-insoluble carrier, and is a conjugate in which the molecule is a molecule capable of capturing a lectin-binding substance and the water-insoluble carrier and the molecule are bound together directly or indirectly.

(Target Substance-Capture Molecule)

In the present invention, a "molecule capable of capturing a lectin-binding substance" a molecule capable of binding to a lectin-binding substance, and capable of capturing the lectin-binding substance as a target substance (hereinafter referred to as a "target substance-capture molecule" in some cases). The target substance-capture molecule is not particularly limited as long as it has an ability to bind to the lectin-binding substance, and may be any of antibodies, binding proteins (such as protein A, protein G, and protein L), receptor proteins, nucleic acids, and the like. The antibody may be an polyclonal antibody or a monoclonal antibody. Further, in the present invention, the "antibodies" include not only complete antibodies but also antibody fragments (for example, Fab, Fab', F(ab')$_2$, Fv, single chain antibody, diabody, and the like) and a low molecular weight antibody to which a variable region of the antibody is bound. In the purification treatment, it is particularly desirable to wash away glycan-containing components other than the target substance. Therefore, it is preferable to exclude any lectin having glycan binding property from the target substance-capture molecule.

In addition, the target substance-capture molecule used in the capturing step according to the present invention may be a molecule that specifically binds only to a glycan portion which the lectin recognizes and binds to (for example, an antibody capable of recognizing and binding to the same site as the lectin does), or may be a molecule capable of recognizing and binding to a portion other than the glycan portion (for example, a protein portion of the glycoprotein or a lipid portion of the glycolipid) or a portion including the glycan portion as a part thereof in the lectin-binding substance. However, the target substance-capture molecule is preferably a molecule capable of recognizing and binding to a portion other than the glycan portion in the lectin-binding substance and is preferably, for example, an anti-protein antibody against the protein portion of the glycoprotein (for example, anti-AFP antibody or anti-PSA antibody). Therefore, the target substance-capture molecule may be a molecule capable of capturing not only a lectin-binding substance (for example, AFP-L3 or PSA (prostate-specific antigen)), but also a substance obtained by excluding, from the lectin-binding substance, the glycan portion which the lectin recognizes and binds to (for example, only a protein portion of AFP, AFP-L1, or PSA). In the present invention, even when a prepared sample obtained contains such a substance in addition to a lectin-binning substance, it is possible to measure the lectin-binding substance with high sensitivity.

The target substance-capture molecule can be produced by employing and modifying a conventionally known production method, or a general commercially available one may be used as appropriate. For example, when a lectin-binding substance AFP-L3, a commercially available anti-AFP monoclonal antibody or the like may be used as appropriate.

(Water-Insoluble Carrier)

The water-insoluble carrier included in the capture carrier of the present invention mainly functions as a carrier that carries and immobilizes the target substance-capture molecule and is made of water-insoluble substance. In the present invention, a "water-insoluble substance" refers to a substance insoluble in water under normal temperature and normal pressure (the solubility in water is 0.001 g/mL or less and is preferably 0.0001 g/mL or less; the same applies below).

As a material for such a water-insoluble carrier, any of materials generally used for immunological measurements can be used without particular limitation. An example thereof is at least one kind selected from the group consisting of high molecular polymers (such as polystyrene, (meth) acrylic acid ester, polymethylmethacrylate, polyimide, and nylon), gelatin, glass, latex, silica, metals (such as gold and platinum), and metal compounds (such as iron oxide, cobalt oxide, and nickel ferrite). In addition, the material for the water-insoluble carrier may be a composite material of some of these or a composite material of any of these substances and another substance, or may be, for example, an organic-inorganic composite material including at least one kind of organic polymer in the group consisting of the high molecular polymers, the gelatin, and the latex listed above, and at least one kind of metal compound in the group consisting of iron oxide (such as spinel ferrite), cobalt oxide, and nickel ferrite. Moreover, the water-insoluble carrier may be surface-modified with an active group such as a carboxy group, an epoxy group, a tosyl group, an amino group, a hydroxy group, an isothiocyanate group, an isocyanate group, an azido group, an aldehyde group, a carbonate group, an allyl group, an aminooxy group, a mal, ide group, or a thiol group.

Further, in the present invention, the form of the water-insoluble carrier is not particularly limited, and may be in any of forms such as, for example, a plate, fibers, a membrane, or particles. From the viewpoint of reaction efficiency, the particles are preferable. From the viewpoint of automation and shortening of time, magnetic particles are more preferable. As such a water-insoluble carrier, a conventionally known one can be used as appropriate, or a commercially available one can also be used as appropriate (Structure and Production Method of Capture Carrier)

In the capture carrier of the present invention, the content of the target substance-capture molecule is not particularly limited, and can be adjusted as appropriate depending on the ease of binding between the target substance-capture molecule and the lectin-binding substance or the like. For example, the mass of the target substance-capture molecule (in the case of a combination of two or more kinds of target substance-capture molecules, the total of them) with respect to 100 parts by mass of the water-insoluble carrier (preferably particles) (in the case of combination of two or more kinds of water-insoluble carriers, the total of them) is preferably 0.1 to 10 parts by mass and more preferably 1 to 5 parts by mass.

The capture carrier of the present invention can be produced by immobilizing the target substance-capture molecule on the water-insoluble carrier. As such a production method, a conventionally known method or a method according to it may be used as appropriate, and the target substance-capture molecule may be directly or indirectly immobilized on the water-insoluble carrier. In the case of direct immobilization, for example, the water-insoluble carrier and/or the target substance-capture molecule having active groups such as a carboxy group, an epoxy group, a tosyl group, an amino group, a hydroxy group, an isothiocyanate group, an isocyanate group, an azido group, an aldehyde group, a carbonate group, an allyl group, an aminooxy group, a maleimide group, and a thiol group are(is) used, or the above active groups are added to them as needed, and the target substance-capture molecule can be directly immobilized on the water-insoluble carrier by binding these active groups. In the case of indirect immobilization, for example, a linker that binds to the target substance-capture molecule is immobilized on the water-insoluble carrier and the target substance-capture molecule is bound to the linker, so that the target substance-capture molecule can be indirectly immobilized on the water-insoluble carrier. The linker is not particularly limited, and examples thereof include a secondary antibody capable of binding to the target substance-capture molecule, protein G, protein A, a photo degradable photocleavable linker, a linker molecule having the active group listed above (for example, hydrazine salt, hydrazide, AMAS N-α-maleimidoacet-oxysuccinimide ester), BMPS (N-β-maleimidopropyl-oxysuccinimide ester), GMBS (N-γ-maleimidobutyryl-oxysuccinimide ester), MBS (m-maleimidobenzoyl-N-hydroxysuccinimide ester), SMCC (succinimidyl 4-(N-maleimidomethyl)cyclohexane-1-carboxylate), EMCS (N-ε-malemidocaproyi-oxysuccinimide ester), SMPB (succinimidyl 4-(p-maleimidophnyl)butyrate), SMPH (Succinimidyl 6-((beta-maleimidopropionamido)hexanoate)), LC-SMCC (succinimidyl 4-(N-maleimidomethyl)cyclohexane-1-carboxy-(6-amidocaproate)), Sulfo-KMUS (N-κ-maleimidoundecanoyl-oxysulfosuccinimide ester), SIA (succinimidyl iodoacetate), SBAP (succinimidyl 3-(bromoacetamido)propionate), SIAB (succinimidyl (4-iodoacetyl)aminobenzoate), Sulfo-SANPAH (sulfosuccinimidyl 6-(4'-azido-2'-nitrophenylamino)hexanoate), SDA (succinimidyl 4,4'-azipentanoate), Sulfo-SDAD (sulfosuccinimidyl 2-((4,4'-azipentanamido)ethyl)-1,3'-dithiopropionate), EDC (1-ethyl-3-(3-dimethylaminopropyl)carbodiimide hydrochloride), NHS (N-hydroxysuccinimide), BMPH (N-β-maleimidopropionic acid hydrazide), EMCH (N-ε-maleimidocaproic acid hydrazide), MPBH (4-(4-N-maleimidophenyl) butyric acid hydrazide), KMUH (N-κ-maleimidoundecanoic acid hydrazide), PDPH (3-(2-pyridyldithio)propionyl hydrazide), PMPI (p-maleimidophenyl isocyanate), and SPB (succinimidyl-[4-(psoralen-8-yloxy)]-butyrate)), and the like. Further, the target substance-capture molecule may be immobilized on the water-insoluble carrier by modifying the target substance-capture molecule in some way and immobilizing a substance that captures the modified portion of the target substance-capture molecule on the water-insoluble carrier. For example, a typical example of the above modified portion is biotin and a typical example of the substance that captures the modified portion is streptavidin. However, the modified portion and the substance are not limited to these. A ratio between the water-insoluble carrier and the target substance-capture molecule provided for these reactions can be selected as appropriate so as to achieve the preferable range of the ratio in the capture carrier described above. In addition, if necessary, blocking of the water-insoluble carrier may be performed by using an appropriate blocking agent (for example, such as bovine serum albumin or gelatin) for the purpose of preventing non-specific adsorption to the target substance-capture molecule and the water-insoluble carrier. Further, as such a capture carrier, for example, a commercially available carrier such as anti-AFP antibody-binding particles or anti-PSA antibody-binding particles may be used as appropriate.

<Lectin-Binding Substance Measurement Method>

In a lectin-binding substance measurement method of the present invention, the following purification treatment using the aforementioned capture carrier of the present invention is performed on a sample before a lectin-binding substance in the sample is measured by using a lectin.

[Purification Treatment]

The purification treatment of the present invention includes a capturing step of bringing the capture carrier into contact with the sample to cause the capture carrier to capture the lectin-binding substance; a washing step of removing contaminants unbound to the capture carrier; and a releasing step of releasing the lectin-binding substance from the capture carrier to obtain a prepared sample (Capturing Step)

In the capturing step, the capture carrier is brought into contact with the sample and thereby is caused to capture the lectin-binding substance through binding between the lectin-binding substance and the target substance-capture molecule. A method for bringing the capture carrier into contact with the sample is not particularly limited, and a conventionally known method or a method according to it can be used as appropriate. For example, in the case where the water-insoluble carrier is a plate and the capture carrier is a target substance-capture molecule-immobilized plate, there is a method for injecting the sample into this plate. In the case where the water-insoluble carrier is particles and the capture carrier is target substance-capture molecule-immobilized particles, there is a method for adding the target substance-capture molecule-immobilized particles to the sample.

The sample may be diluted with a sample diluent and used. In the case where the capture carrier is the target substance-capture molecule-immobilized particles, the these particles may be diluted in a particle suspension medium of these particles and used. In addition, another buffer for reaction may be added to a reaction system of the capture carrier and the sample (for example, an antigen-antibody reaction system) as appropriate. These sample diluent, particle suspension medium, and buffer for reaction are not particularly limited, and, for example, may be each independently any of known buffers (such as sodium phosphate buffer, MES, Tris, CFB, MOPS, PIPES, HEPES, tricine buffer, bicine buffer, and g glycine buffer) The particle suspension medium and the buffer for reaction may be each independently added with a stabilizing protein such as BSA, serum, or the like.

In the reaction between the capture carrier and the sample in the capturing step, the content (final concentration) of the capture carrier (in the case of a combination of two or more kinds of capture carriers, the total of them; the same applies below) in the reaction solution containing the capture carrier and the sample is not particularly limited. Although the content of the capture carrier is not particularly limited because it is appropriately adjusted according to the kind, concentration, purpose of the purification treatment, and the like of the sample, the content for example, preferably 0.01 to 1.5% by mass, more preferably 0.05 to 1% by mass, and further preferably 0.1 to 0.5% by mass from the viewpoint of efficiently recovering the substance captured by the target substance-capture molecule within a short period of time.

In addition, the conditions in the capturing step are not particularly limited and can be adjusted as appropriate. For example, the capturing step may be performed at room temperature to 45° C. or preferably 20° C. to 37° C., at a pH of about 6 to 9 or preferably a pH 7 to 8, for about 5 seconds to 10 minutes or preferably about 30 seconds to 5 minutes. However the conditions are not limited to these conditions.

(Washing Step)

In the washing step, a target substance (including at least a lectin-binding substance in the case where the sample contains the lectin-binding substance) bound to the capture carrier and other contaminants unbound to (not captured by) the capture carrier are separated from each other and the contaminants are removed. A method for removing the contaminants is not particularly limited, and a conventionally known method or a method according to it can be used as appropriate. For example, in the case where the water-insoluble carrier is a plate and the capture carrier is a target substance-capture molecule-immobilized plate, there is a method for removing a liquid phase (supernatant) from the plate after the aforementioned capturing step. In the case where the water-insoluble carrier is particles and the capture carrier is target substance-capture molecule-immobilized particles, there is a method for collecting the particles by centrifugation or magnetic collection after the aforementioned capturing step, and then removing the liquid phase (supernatant). In the washing step, thereafter, injection and removal of a washing liquid may be repeated as needed. Examples of the washing liquid include neutral (preferably a pH of 6 to 9) known buffers (such as sodium phosphate buffer, MES, Tris, CFB, MOPS, PIPES, HEPES, tricine buffer, bicine buffer, and glycine buffer), and the washing liquid may be added with a stabilizing protein such as BSA, a surfactant, or the like.

(Releasing Step)

In the releasing step, the lectin-binding substance bound to the capture carrier is released from the capture carrier to obtain a prepared sample containing the re-released lectin-binding substance as a sample for use in the measuring step. A method for releasing the lectin-binding substance from the capture carrier is not particularly limited, and may be a method for acidifying or alkalinizing the reaction system; a method for cleaving a photocleavable linker by light irradiation in the case where the photocleavable linker is used as the linker; a method using a surfactant; a method using a protein denaturing agent; a method for applying heat; a method using a combination of the above methods; or the like.

For example, in the case of acidifying the reaction system, there is method for bringing an eluate preferably having a pH of 4 or less (more preferably, a pH of 3 to 1) into contact with the capture carrier to which the lectin-binding substance is bound. In the case of alkalinizing the reaction system, there is a method for bringing an eluate preferably having a pH of 9 or more (more preferably, a pH of 10 to 14) into contact with the capture carrier.

The eluate is one containing an acidifying agent (for example, hydrochloric acid, sulfuric acid, acetic acid, or citric acid), an alkalizing agent (for example, sodium hydroxide, potassium hydroxide, or magnesium hydroxide), or the like. In these cases, after that, it is preferable to neutralize the reaction system by adding a neutralizing agent (for example, hydrochloric acid, sulfuric acid, acetic acid, citric acid, sodium hydroxide, potassium hydroxide, magnesium hydroxide, or a known buffer solution prepared to be alkaline or acidic) or the like to the eluate.

The other conditions in the releasing step are not particularly limited and can be adjusted as appropriate depending on the method. For example, the releasing step may be performed at room temperature to 37° C. or preferably 20° C. to 37° C. for about 5 seconds to 10 minutes or preferably about 30 seconds to 5 minutes. However, the conditions are not limited to these conditions.

[Measuring Step]

Regarding a prepared sample obtained by the purification treatment, the lectin-binding substance measurement method of the present invention includes measuring a lectin-binding substance in the prepared sample by using a lectin. In the present invention, "measurement" includes detection for confirming the presence or absence of a lectin-binding substance, as well as quantification or semi-quantification of the amount of the lectin-binding substance. In the present invention, the measurement of the lectin-binding substance is performed by detecting a signal generated by the labeling substance and quantifying the detected signal as needed. The above-mentioned "signal" includes coloration (color development), reflected light, light emission, fluorescence, radiation by a radioisotope, and the like, and includes not only signals which can be checked with the naked eyes but also signals which can be checked by a measurement method/device depending on the type of the signal.

The method for measuring the lectin-binding substance by using a lectin is not particularly limited as long as it is a method utilizing the affinity between the lectin and the lectin-binding substance. As a principle of the measurement method for measuring a lectin-binding substance of the present invention, any of the same principles as the sandwich method, the competitive method, the immunoturbidimetry method and the like in the immunological measurement methods can employed. In the lectin-binding substance measurement method of the present invention, the quantification of the lectin-binding substance in the sample can be generally performed by employing a method in which a microplate, particles, or the like is used as a carrier, such as ELISA, digital ELISA, CLEIA (chemiluminescent enzyme immunoassay), CLIA (chemiluminescent immunoassay), ECLIA (electro chemiluminescent immunoassay), or RIA (radioimmunoassay), performing detection and quantification depending on a kind of the labeling substance, and comparing the obtained value with the measured value in a standard sample. On the other hand, from the viewpoint of detecting the lectin-binding substance more easily and quickly, for example, a method such as immunochromatography can be employed as the sandwich method.

As the lectin-binding substance measurement method of the present invention, a method preferable from the viewpoint that the method tends to enable construction of a detection system with higher sensitivity and higher specificity is the sandwich method which uses a trap capable of capturing a lectin-binding substance and a detectable substance (label) containing a labelling substance. As the sandwich method, there are a two-step forward sandwich method (a reaction between the trap and the lectin-binding substance in the sample, and a reaction between the lectin-binding substance bound to the trap and the detectable substance are performed sequentially), a reverse sandwich method (the detectable substance is reacted with the lectin-binding substance in the sample in advance, and the generated complex is reacted with the trap), and a one-step method (the reactions between the trap, the lectin-binding substance in the sample, and the detectable substance are performed concurrently in one step). Any of these methods may be employed.

More preferably, for example, the aforementioned forward sandwich method may be performed as follows. First, an antibody capable of capturing a lectin-binding substance is used as a trap (capture antibody), and a water-insoluble carrier on which the antibody is immobilized is brought into contact with and bound to the lectin-binding substance in the sample (primary reaction step). After that, the lectin-binding substance unbound to the capture antibody and contaminants are removed with an appropriate washing liquid (for example, a buffer solution or the like) as needed. Next, the detectable substance is brought into contact with and bound to the lectin-binding substance captured by the capture antibody (secondary reaction step), As a result of this reaction, an immune complex containing the capture antibody—the lectin-binding substance—the detectable substance is formed on the water-insoluble carrier. The detectable substance unbound is washed away with a washing liquid, a d then the labeling substance in the detectable substance is measured by a predetermined method. For example, when the labeling substance contained in the detectable substance is an enzyme, a color-developing substrate or a luminescent substrate specific to the enzyme is added, and a signal generated by a reaction of the enzyme with the substrate is measured.

As the "antibody capable of capturing a lectin-binding substance" for use in the aforementioned sandwich method, the same antibodies as listed above in the target substance-capture molecule contained in the capture carrier can be used. From the viewpoint of further enhancing the measurement accuracy, the antibody capable of capturing a lectin-binding substance for use in the measuring step is not an antibody that specifically binds only to a glycan portion which the lectin recognizes and binds to (that is, an antibody that recognizes or physically covers and binds to the same site as the lectin does), or an antibody that recognizes and binds to a portion including the glycan portion as a part thereof, but is preferably an antibody that recognizes and binds to a portion other than the glycan portion (for example, protein portion of the glycoprotein or a lipid portion of the glycolipid) in the lectin-binding substance. In addition, an antibody not having a glycan structure that the lectin recognizes, for example, such as Fab, Fab', or F(ab')$_2$ fragment is also preferable. Moreover, as the antibody capable of capturing a lectin-binding substance for use in the measuring step, a complete antibody may be used. However, it cannot be denied that the complete antibody having a glycan structure may cause a non-specific reaction with the lectin and increase the background. For this reason, it is more preferable to prepare antigen-binding fragments not having a glycan structure or destroy the glycans on the antibody in advance.

In addition, the "water-insoluble carrier" for use in the above sandwich method is not particularly limited as long as it is capable of immobilizing and carrying the antibody and is insoluble in water under normal temperature and normal pressure, and it is possible to use the same carriers as listed above as the water-insoluble carrier contained in the aforementioned capture carrier.

The "water-insoluble carrier on which the capture antibody is immobilized" for use in the above sandwich method can be produced in the same manner as the method for immobilizing the target substance-capture molecule on the water-insoluble carrier in the capture carrier production method described above.

As a method for the above contact in the lectin-binding substance measurement method of the present invention, a conventionally known method or a method according to it can be used as appropriate. For example, in the case where the water-insoluble carrier is a plate, there is a method for injecting the prepared sample and the detectable substance into this plate. In the case where the water-insoluble carrier is particles, there is a method for mixing the particle solution, the prepared sample, and a solution of the detectable substance with each other at one time or sequentially. In the case where the above water-insoluble carrier is particles, the prepared sample may be suspended in a particle suspension medium and used. In addition, another buffer for reaction may be added as appropriate to a reaction system of the trap (capturing antigen), the detectable substance, and the prepared sample. These particle suspension medium and buffer for reaction may be the same as listed in the purification treatment described above, and each can be selected as appropriate without particular limitation.

As preferred modes of the measuring step in the lectin-binding substance measurement method of the present invention, there are, for example, a method using a blocked labeled lectin (first mode), a method using a labeled lectin (second mode), and a combination of these (third mode), which will be described below.

(First Mode)

In the first mode of the lectin-binding substance measurement method of the present invention, the measuring step includes a step of bringing a blocked labeled lectin including a water-soluble carrier made of a first water-soluble polymer and a labeling substance and a lectin immobilized on the water-soluble carrier into contact with the prepared sample.

In the first mode, the "blocked labeled lectin" is a complex including a water-soluble carrier made of a water-soluble polymer and a labeling substance and a lectin immobilized on the water-soluble carrier and is a conjugate in which the water-soluble carrier, the labeling substance, and the lectin bind to each other directly or indirectly. The blocked labeled lectin of the present invention only has to be such that the labeling substance and the lectin are carried on the water-soluble carrier. The labeling substance and the lectin may bind to the water-soluble carrier independently of each other, any one of the water-soluble carrier, the labeling substance, and the lectin may bind to the other two, the lectin may bind to the water-soluble carrier via the labeling substance, the labeling substance may bind to the water-soluble carrier via the lectin.

(Water-Soluble Carrier)

The water-soluble carrier included in the blocked labeled lectin of the present invention mainly functions as a carrier that carries the labeling substance and the lectin, and is made of a water-soluble polymer. The water-soluble polymer (hereinafter referred to as a "first water-soluble polymer") constituting the water-soluble carrier according to the present invention is not particularly limited as long as it is a water-soluble polymer capable of immobilizing and carrying the labeling substance and the lectin. In the present invention, the "water-soluble polymer" refers to a polymeric compound in which the solubility in water under normal temperature and normal pressure is more than 0.01 g/mL, is preferably 0.05 g/mL, or more, and is more preferably 0.1 g/mL or more.

The first water-soluble polymer according to the present invention has a weight average molecular weight (a polystyrene-equivalent weight average molecular weight measured by gel permeation chromatography (GPC); the same applies below) of preferably 6,000 to 4,000,000 and more preferably 20,000 to 1,000,000 from the viewpoints of the measurement sensitivity and water-solubility. Furthermore, from the viewpoint that there is a tendency to enable a lectin-binding substance, which is a measurement target substance, to be measured with higher sensitivity even when the concentration of the lectin-binding substance is low, the first water-soluble polymer preferably has a high molecular weight, and has a weight average molecular weight of preferably 20,000 to 1,000,000 and more preferably 50,000 to 700,000.

Moreover, the blocked labeled lectin of the present invention is also preferably a combination of a high molecular weight blocked labeled lectin in which the first water-soluble polymer has a weight average molecular weight of 200,000 or more and a low molecular weight blocked labeled lectin in which the first water-soluble polymer has a weight average molecular weight of less than 100,000 (more preferably 100,000 or less) and is more preferably a combination of a high molecular weight blocked labeled lectin in which the first water-soluble polymer has a weight average molecular weight of 200,000 to 700,000 (further preferably 250,000 to 500,000) and a low molecular weight blocked labeled lectin in which the first water-soluble polymer has a weight average molecular weight of 20,000 to 100,000 (further preferably 50,000 to 70,000). When the high molecular weight blocked labeled lectin and the low molecular weight blocked labeled lectin are combined, a measurable concentration range of a lectin-binding substance, which is a measurement target substance, tends to be widen more. The present inventors presume that this is because the low molecular weight blocked labeled lectin is inserted into the high molecular weight blocked labeled lectin and the blocked labeled lectin has a higher density.

In addition, in the case where the high molecular weight blocked labeled lectin and the low molecular weight blocked labeled lectin are combined as the blocked labeled lectin of the present invention, a mass ratio between them (the mass of the high molecular weight blocked labeled lectin:the mass of the low molecular weight blocked labeled lectin) is preferably 10:1 to 1:10, more preferably 5:1 to 1:5, and further preferably 3:1 to 1:3.

Moreover, as the blocked labeled lectin of the present invention, one blocked labeled lectin may contain, as the first water-soluble polymer, multiple kinds of water-soluble polymers different in the weight average molecular weight.

Examples of the first water-soluble polymer according to the present invention include: polysaccharides such as dextran, aminodextran, Ficoll (trade name), dextrin, agarose, purulan, various celluloses (for example, hemicellulose, lignin, and so on), chitin, and chitosan; β-galactosidase; thyroglobulin; hemocyanin; polylysine; polypeptide; DNA; and modified products of these (for example, diethylaminoethyl dextran, dextran sodium sulfate, and so on). The first water-soluble polymer may be one kind of these alone or a combination of two or more kinds of these. From the viewpoints that a large quantity is obtainable with low cost and chemical treatments such as addition of a functional group and a coupling reaction are relatively easy, the first water-soluble polymer according to the present invention is preferably at least one kind selected from the group consisting of polysaccharides and modified products thereof among the above, is more preferably at least one kind selected from the group consisting of dextran, aminodextran, and the modified products thereof, and is further preferably dextran.

(Labeling Substance)

The labeling substance included in the blocked labeled lectin of the present invention mainly functions as a label for the blocked labeled lectin, and any of labeling substances used in the known immunological measurements may be used without particular limitation.

Examples of the labeling substance according to the present invention include enzymes; luminescent substances such as acridinium derivatives; fluorescent substances such as europium; fluorescent proteins such as allophycocyanin (APC) and phycoerythrin (R-PE); radioactive substances such as $^{125}$I; low molecular weight labeling substances such as fluorescein isothiocyanate (FITC) and rho amine isothiocyanate (RITC); gold particles; avidin; biotin; latex; dinitrophenyl (DNP); and digoxigenin (DIG) The labeling substance may be one kind of these alone or a combination of two or more kinds of these. When an enzyme is used as the labeling substance, for example, a color-developing substrate, a fluorescent substrate, a chemiluminescent substrate, or the like is added as a substrate, so that it is possible to conduct detection and quantification of any of various substances depending on the substrate. Examples of the enzyme include, but not limited to, horseradish peroxidase (HRP), alkaline phosphatase (ALP), β-galactosidase (β-gal), glucose oxidase, and luciferase.

(Lectin)

Examples of the lectin included in the blocked labeled lectin of the present invention include lectins listed in the above lectin-binding substance. The lectin is not particularly limited, can be selected depending on a kind of a lectin-binding substance, which is a measurement target substance, and may be one kind alone or a combination of two or more kinds. Among them, the lectin included in the blocked labeled lectin of the present invention is preferably at least one kind selected from the group consisting of *Lens culinaris* agglutinin (LCA), *Maackia amurensis* lectin (MAM), *Aleuria aurantia* lectin (AAL), and *Wisteria floribunda* agglutinin (WFA) and is more preferably one kind selected from these from the viewpoint that glycoprotein measurement based on cancer-specific glycoforms appearing on proteins is used to assist in the diagnosis of a malignant tumor.

(Structure and Production Method of Blocked Labeled Lectin)

In the blocked labeled lectin of the present invention, the content of the labeling substance is not particularly limited and can be adjusted as appropriate depending on a measurement mechanism or the like. In order to more improve the measurement sensitivity, however, the content the labeling substance is preferably set such that the number of molecules of the labeling substance binding to one molecule of the first water-soluble polymer is as large as possible. For example, when the labeling substance is an enzyme, the mass of the labeling substance (in the case of a combination of two or more kinds of labeling substances, the total of then) with respect to 100 parts by mass of the first water-soluble polymer (in the case of a combination of two or more kinds of first water-soluble polymers, the total of them; the same applies below) is preferably 100 to 1,000 parts by mass, and more preferably 300 to 800 parts by mass.

In the blocked labeled lectin the present invention, the content of the lectin is not particularly limited. In order to more improve the measurement sensitivity, however, the content of the lectin is preferably set such that the number of molecules of the lectin binding to one molecule of the first water-soluble polymer is as large as possible. For example, the mass of the lectin (in the case of a combination of two or more kinds of lectins, the total of them) with respect to 100 parts by mass of the first water-soluble polymer is preferably 100 to 2,000 parts by mass and more preferably 300 to 1,500 parts by mass.

As the blocked labeled lectin of the present invention, the weight average molecular weight per molecule of the blocked labeled lectin is preferably 1,000,000 to 10,000,000 and more preferably 1,500,000 to 5,000,000, When the weight average molecular weight is 1,000,000 or more, the measurement sensitivity tends to become higher. On the other hand, when the weight average molecular weight is 10,000,000 or less, flocculation or the like in an aqueous solution tends to be sufficiently inhibited.

The blocked labeled lectin of the present invention can be produced by immobilizing the labeling substance and the lectin on the water-soluble carrier. As such a production method, a conventionally known method or a method according to it may be used as appropriate, and the labeling substance and the lectin (hereinafter, collectively referred to as the "carried substance" in some cases) may be directly or indirectly immobilized on the water-soluble carrier.

As a method for directly immobilizing the carried substance on the water-soluble carrier, for example, there is a method in which active groups such as a carboxy group, an epoxy group, a tosyl group, an amino group, a hydroxy group, an isothiocyanate group, an isocyanate group, an azido group, an aldehyde group, a carbonate group, an allyl group, an aminooxy group, a maleimide group, a thiol group, and a pyridyl disulfide group are added to the carried substance and/or the first water-soluble polymer constituting the water-soluble carrier, or water-soluble polymers having these active groups are used as the carried substance and/or the water-soluble carrier, and the carried substance is immobilized on the water-soluble carrier by covalent bonds using these active groups. As the carried substance and the first water-soluble polymer to which the above active groups are added, commercially available ones may be used as they are, or the carried substance and the water-soluble polymer may be prepared by introducing the above active groups into the surfaces thereof under appropriate reaction conditions. As one example, the thiol group can be introduced by using a commercially available reagent such as, for example, S-acetylmercaptosuccinic anhydride or 2-iminothiolane hydrochloride. In addition, a maleimide group may be introduced to an amino group on the carried substance and/or the first water-soluble polymer constituting the water-soluble carrier by using a commercially available reagent such as, for example, N-(6-maleimide caproyloxy) succinimide or N-(4-maleimide butyryloxy) succinimide. A pyridyl disulfide group may be introduced by using a commercially available reagent such as, for example, N-succinimidyl 3-(2-pyridyldithio)propionate (SPDP), N-{6-[3-(2-pyridyldithio)propionamido]hexanoyloxy} sulfosuccinimide, or sodium salt (Sulfa-AC5-SPDP). Moreover, a thiol group may be introduced by introducing a pyridyl disulfide group and then reducing this to the thiol group.

As a method for indirectly immobilizing the carried substance on the water-soluble carrier, there is a method for immobilization via a linker such as, for example, polyhistidine, polyethylene glycol, oligopeptide containing cysteine and/or lysine, and a linker molecule having the above active group (for example, hydrazine salt, hydrazide, AMAS, BMPS, GMBS, MES, SMCC, EMCS, SMPB, SMPH, LC-SMCC, Sulfo-KMUS, SIA, SBAP, STAB, Sulfo-SANPAH, SDA, Sulfo-SDAD, EDC, NHS, BMPH, EMCH, MPBH, KMUH, PDPH, PMPI, and SPE), and the like. The selection and the size of the linker may be set as appropriate in consideration of the strength of binding to the carried substance, steric hindrance due to immobilization of the carried substance on the water-soluble carrier, and so on.

In the method for producing the blocked labeled lectin of the present invention, the labeling substance and the lectin may be immobilized on the water-soluble carrier at one time, or immobilized separately one by one. From the viewpoint of the ease of production and the ease of control of the amounts of the labeling substance and the lectin, it is preferable to immobilize one of the labeling substance and the lectin on the water-soluble carrier first, and then to immobilize the other thereon.

Moreover, the blocked labeled lectin of the present invention can be produced by immobilizing the labeling substance and the lectin on different water-soluble carriers respectively, and binding the labeling substance immobilized on one of the water-soluble carriers (blocked labeling substance) and the lectin immobilized on the other water-soluble carrier (blocked lectin) directly or via the above linker or the like.

Such a production method is not particularly limited. When the labeling substance is an enzyme and the first water-soluble polymer is polysaccharide or glycoprotein as in Reference Examples to be described later in Examples, the first water-soluble polymer is first oxidized with an oxidizing accent such as sodium periodate to add an aldehyde group, is reacted with hydrazine hydrochloride, and then is reduced with a reducing agent such as dimethylamine borane (DMAB) to be hydrazinated. On the other hand, the enzyme is also oxidized with an oxidizing agent such as sodium periodate to add an aldehyde group to the glycan thereof. Next, the hydrazine residue and the aldehyde group added above are reacted to form a hydrazone bond, thereby obtaining a first water-soluble polymer-enzyme conjugate. The obtained first water-soluble polymer-enzyme conjugate is treated with a crosslinker having an N-hydroxysuccinimide and a maleimide group at terminals (for example, such as $SM(PEG)_4$ or SMCC) to introduce the maleimide group. On the other hand, the lectin is thiolated with a thiolation reagent to add a thiol group, the lectin, if having a disulfide bond in the molecule, is reduced to obtain a thiol group. Finally, the maleimide group introduced in the first water-soluble polymer-enzyme conjugate and the thiol group added to the lectin are bound together, so that three substances, that is, the first water-soluble polymer (water-soluble carrier)-enzyme-lectin, can be covalently bonded, With this method, it is possible to obtain a blocked labeled lectin in which the lectin binds to two or more molecules of the first water-soluble polymer which bind to each other via the enzyme. The ratio of the first water-soluble polymer, the labeling substance, and the lectin provided for these reactions may be selected as appropriate so as to achieve the preferable ranges of the contents of them in the blocked labeled lectin described above, (Measurement Method in First Mode)

The first mode of the present invention is preferably a method using the blocked labeled lectin as the detectable substance. In the first mode of the present invention, the content (final concentration) of the blocked labeled lectin (in the case of a combination of two or more kinds of blocked labeled lectins, the total of them; the same applies below) in a reaction solution containing the blocked labeled lectin and the lectin-binding substance in the measuring step, that is, in the reaction between the blocked labeled lectin and the lectin-binding substance is not particularly limited. Although the content of the blocked labeled lectin is not particularly limited because it may be adjusted as appropriate depending on the kind, concentration, and the like of the sample, the content is, for example, preferably 0,001 to 10 μg/mL, more preferably 0.01 to 5 μg/mL, and further preferably 0.1 to 1 μg/mL from the viewpoint that there is a possibility that the blocked labeled lectin, if used excessively, may generate a high background signal.

In the first mode of the present invention, the other conditions in the measuring step are not particularly limited, and can be adjusted as appropriate. For example, the reaction between the blocked labeled lectin and the lectin-binding substance can be performed at room temperature to 37° C. or preferably 20° C. to 37° C., at a H of 5.0 to 7.0 or preferably to 6.5, for about 3 minutes to 120 minutes or preferably about 5 minutes to 10 minutes. However, the conditions are not limited to these conditions.

(Second Mode)

In the second mode of the lectin-binding substance measurement method of the present invention, the measuring step includes a step of bringing a labeled lectin including a labeling substance and a lectin into contact with the prepared sample.

In the second mode, the "labeled lectin" is a complex containing a labeling substance and a lectin and is a conjugate in which the labeling substance and the lectin bind to each other directly or indirectly. The labeled lectin is different from the blocked labeled lectin in the first mode in that the labeled lectin does not include the water-soluble carrier.

The labeling substance contained in the labeled lectin may be any of the same substances as listed as the labeling substance contained in the blocked labeled lectin in the first mode and may be one of these alone or a combination of two or more of these. In the case where the labeled lectin is used in combination with the blocked labeled lectin, the labeling substance in the labeled lectin may be the same kind as the labeling substance contained in the blocked labeled lectin.

The lectin contained in the labeled lectin may be any of the same lectins as listed as the lectin contained in the blocked labeled lectin in the first mode and may be one of these alone or a combination of two or more of these. In the case where the labeled lectin is used in combination with the blocked labeled lectin, the lectin in the labeled lectin may be the same kind as the blocked labeled lectin. Among these, the lectin contained in the labeled lectin is preferably at least one kind selected from the group consisting of *Lens culinaris* agglutinin (LCA), *Maackia amurensis* lectin I (MAM), *Aleuria aurantia* lectin (AAL), and *Wisteria floribunda* agglutinin (WFA), and is more preferably any one kind of these.

The content ratio between the labeling substance and the lectin in the labeled lectin is not particularly limited, and can be adjusted as appropriate depending on a measurement mechanism and so on. However, for example, when the labeling substance is an enzyme, the content ratio between the labeling substance and the lectin (the mass of labeling substance:the mass of the lectin; in the case of a combination of two or more kinds of labeling substances and a combination of two or more kinds of lectins, the total of the labeling substances and the total of the lectins independently) is preferably 50:1 to 1:50, more preferably 10:1 to 1:10, and further preferably 5:1 to 1:5.

The labeled lectin can be produced by binding the labeling substance and the lectin to each other. As such a production method, a conventionally known method or a method according to it may be used as appropriate, and the labeling substance and the lectin may be directly or indirectly immobilized. As such a method, the same method as described as the method for producing the blocked labeled lectin in the first mode may be used. The ratio between the labeling substance and the lectin provided for these reactions may be selected as appropriate so as to achieve the preferable content ratio described above.

(Measurement Method in Second Mode)

The second mode of the present invention is preferably a method using the labeled lectin as the detectable substance. In the second mode of the present invention, the content (final concentration) of the labeled lectin (in the case of a combination of two or more kinds of labeled lectins, the total of them; the same applies below) in a reaction solution containing the labeled lectin and the lectin-binding substance in the measuring step, that in the reaction between the labeled lectin and the lectin-binding substance is not particularly limited. Although the content of the labeled lectin is not particularly limited because it may be adjusted as appropriate depending on the kind, concentration, and the like of the sample, the content is, for example, preferably 0.001 to 10 µg/mL, more preferably 0.01 to 5 µg/mL, and further preferably 0.1 to 1 µg/mL from the viewpoint that there is a possibility that the labeled lectin, if used excessively, may generate a high background signal.

In the second mode of the present invention, the other conditions in the measuring step are not particularly limited, and can be adjusted as appropriate. For example, the reaction between the labeled lectin and the lectin-binding substance can be performed at room temperature to 3'7° C. or preferably 20° C. to 37° C., at a pH of 5.0 to 7.0 or preferably 5.5 to 6.5, for about 3 minutes to 120 minutes or preferably about 5 minutes to 10 minutes. However, the conditions are not limited to these.

(Third Mode)

In the third mode of the lectin-binding substance measurement method of the present invention, the measuring step includes a step of bringing the blocked labeled lectin and the labeled lectin into contact with the prepared sample. In the third mode of the lectin-binding substance measurement method of the present invention, the coexistence of the blocked labeled lectin and the labeled lectin in the measuring step makes it possible to further improve the measurement sensitivity. The present inventors presume that this is because the excessive existence of the lectin labeled by the reaction system more promotes the reaction between the lectin-binding substance and the blocked labeled lectin in the binding direction and the low-molecular labeled lectin can bind to the lectin-binding substance to which the high-molecular blocked labeled lectin cannot bind due to a steric hindrance.

The blocked labeled lectin, the labeled lectin, and the measurement method using these are the same as described in the first mode and the second mode. The lectins contained in the blocked labeled lectin and the labeled lectin are preferably the same kind. In addition, in the third mode, the blocked labeled lectin and the labeled lectin may be mixed in advance or the solutions thereof and the prepared sample may be mixed at one time. In this case, the amounts of the blocked labeled lectin and the labeled lectin are not particularly limited, but the content of the labeled lectin (in the case of a combination of two or more kinds of labeled lectins, the total of them) in a reaction solution containing the prepared sample, the blocked labeled lectin, and the labeled lectin with respect to 100 parts by mass of the content of the blocked labeled lectin is preferably 1 to 1,000 parts by mass and more preferably 10 to 500 parts by mass.

(Second Water-Soluble Polymer)

In the first to third modes of the present invention, the measuring step, that is, the reaction between the blocked labeled lectin and/or the labeled lectin and the lectin-binding substance is preferably performed in the presence of a water-soluble polymer, in other words, under a condition where the water-soluble polymer, the blocked labeled lectin and/or the labeled lectin, and the prepared sample (lectin-binding substance) coexist.

Unlike the first water-soluble polymer constituting the water-soluble carrier, the water-soluble polymer that preferably coexists with the blocked labeled lectin and/or the labeled lectin is a free water-soluble polymer (referred to as second water-soluble polymer below) carrying none of the labeling substance and the lectin. In the first to third modes of the present invention, the measurement sensitivity can be further improved when the second water-soluble polymer coexists in the measuring step.

The second water-soluble polymer may be any of the same polymers as listed as the first water-soluble polymer, and may be one kind of these alone or a combination of two or more kinds of these. The second water-soluble polymer may be the same kind of polymer as the first water-soluble polymer. Among these, the second water-soluble polymer is preferably at least one kind selected from the group consisting of polysaccharides and modified products thereof, more preferably at least one kind selected from the group consisting of dextran, aminodextran, and modified products thereof, and further preferably dextran from the viewpoint of the tendency to more improve the measurement sensitivity.

In addition, from the viewpoint of the tendency to more improve the measurement sensitivity, the weight average molecular weight of the second water-soluble polymer is preferably 500,000 to 5,000,000, more preferably 000,000 to 3,000,000, and further preferably 1,500,000 to 2,500,000.

In the case where the second water-soluble polymer coexists in the measuring step, the second water-soluble polymer may be added to the prepared sample in advance or added to a solution of the blocked labeled lectin and/or the labeled lectin advance, or a solution of the second water-soluble polymer may be mixed with these. In this case, the amount of the second water-soluble polymer is not particularly limited, but the content of the second water-soluble polymer (in the case of a combination of two or more kinds of second water-soluble polymers, the total of them) in a reaction solution containing the prepared sample, the blocked labeled lectin and/or the labeled lectin (in the case where both of them are contained, the total of them), and the second water-soluble polymer is preferably 0.01 to 10 w/v % and more preferably 0.5 to 3 w/v % (w/v %: weight/volume (g/mL) percent; the same applies below).

(Free Lectin)

In the first to third modes of the present invention, it is also preferable that the measuring step, specifically, the reaction between the blocked labeled lectin and/or the labeled lectin and the lectin-binding substance be performed in the presence of a free lectin, in other words, under the condition where the free lectin, the blocked labeled lectin and/or the labeled lectin, and the prepared sample (lectin-binding substance) coexist.

The free lectin preferably coexisting with the blocked labeled lectin and/or the labeled lectin is a free lectin not immobilized on the water-soluble carrier or the labeling substance unlike the lectin contained in the blocked labeled lectin and the lectin contained in the labeled lectin (hereinafter referred to as the "free lectin"). The lectin-binding substance measurement method using a lectin tends to have high background because the lectin non-specifically binds to substances other than the target substance (for example, a lectin recognizing glycan bound to a protein or the like other than the target). In contrast, in the lectin-binding substance measurement of the present invention, the coexistence of the free lectin in the measuring step makes it possible to more suppress an increase in, the background. The present inventors presume that one of the reasons for this is an appropriate masking effect produced by the free lectin. In addition, when the free lectin coexists, the reactivity of the blocked labeled lectin and/or the labeled lectin is improved in some cases. The present inventors presume that the reason for this is that the apparent valence of the blocked labeled lectin and/or the labeled lectin is increased when the polyvalent tree lectin binds monovalently to the glycan structures of the blocked labeled lectin and/or the labeled lectin or that the parallel reactions of binding and unbinding between the blocked labeled lectin and/or the labeled lectin and the lectin-binding substance incline to the binding due to an increase in the local lectin concentration by the addition of the free lectin.

Such a free lectin may be any of the same lectins as listed above as the lectin, and may be one kind of these alone or a combination of two or more kinds of these. In addition, the free lectin may be the same kind as the lectin contained in the blocked labeled lectin and/or the labeled lectin. From the viewpoints of improving the sensitivity and suppressing the background, the free lectin is preferably at least one kind selected from the group consisting of *Lens culinaris* agglutinin (LCA), *Maackia amurensis* lectin I (MAN), *Aleuria aurantia* lectin (AAL), and *Wisteria floribunda* agglutinin (WFA) among these, is more preferably at least one kind selected from the group consisting of *Lens culinaris* agglutinin (LCA) and *Aleuria aurantia* lectin (AAL), is further preferably any one kind of them, and is particularly preferably the same kind as the lectin contained in the blocked labeled lectin and/or the labeled lectin that are to coexist.

In the case where the free lectin coexists in the measuring step, the free lectin may be added to the prepared sample in advance or added to a solution of the blocked labeled lectin and/or the labeled lectin in advance, or a solution of the free lectin may be mixed with these. In this case, the amount of the free lectin is not particularly limited, but the content of the free lectin (in the case of a combination of two or more kinds of free lectins, the total of them) in reaction solution containing the prepared sample, the blocked labeled lectin and/or the labeled lectin (in the case where both of them are contained, the total of them), and the free lectin with respect to 100 parts by mass of the content of the blocked labeled lectin and/or the labeled lectin is preferably 1 to 10,000 parts by mass and more preferably 10 to 5,000 parts by mass.

<Lectin-Binding Substance Measurement Kit>

A lectin-binding substance measurement kit of the present invention includes at least a capture carrier of the present invention as a constituent reagent. In addition, the lectin-binding substance measurement kit preferably further includes at least one kind selected from the group consisting of the blocked labeled lectin, the labeled lectin, the second water-soluble polymer, and the free lectin. These may be each independently in a solid (powder) form or in a liquid form in which it is dissolved in a buffer solution. In the case of the liquid form, the concentrations of the blocked labeled lectin, the labeled lectin, and the capture carrier in the respective solutions (preparations) are not particularly limited. However, from the viewpoint that non-specific signals tend to increase due to excessive additions in some cases, the concentrations are each independently preferably 0.01 to 10 μg/mL, more preferably 0.1 to 5.0 μg/mL, and further p preferably 0.5 to 3.0 μg/mL. In addition, the concentration of the second water-soluble polymer is preferably 0.01 to 10.0 w/v %, more preferably 0.1 to 5.0 w/v %, and further preferably 0.5 to 3.0 w/v %. Then, the concentration of the free lectin is preferably 1 μg/mL or more, more preferably 10 to 500 μg/mL, and further preferably 50 to 250 μg/mL.

The lectin-binding substance measurement kit of the present invention may further include constituent elements that should be provided for ordinary immunological measurements such as ELISA, CLEIA, or immunochromatography. For example, in the case where the sandwich method is employed as the principle of the measurement method, the lectin-binding substance measurement kit may further include at least one kind selected from the group consisting of a magnetic particle solution containing magnetic beads on which a trap is immobilized (or for immobilizing the trap), a plate on which the trap is immobilized (or for immobilizing the trap), a standard sample reagent (each concentration), a control reagent, the sample diluent, the particle suspension medium, the buffer for reaction, the washing liquid, and a cartridge for dilution.

In the case where the labeling substance is an enzyme, the kit may further include a substrate, a reaction stop solution, and so on necessary for detection and quantification of the labeling substance. Further, the lectin-binding substance measurement kit of the present invention may further include a pretreatment solution for pretreating a sample as needed. In the case where the immunochromatography is employed as the sandwich method, the kit may further include a device necessary for this. Moreover, the lectin-binding substance measurement kit of the present invention may further include an instruction manual for the kit.

EXAMPLES

Hereinafter, the present invention will be described more specifically based on Reference Examples, Examples, and Comparative Examples, but the present invention should not be limited to the following Examples. In Reference Examples, Examples, and Comparative Examples, a sign "%" means weight/volume (w/v: g/mL) percent unless otherwise noted.

Reference Example 1

Measurement of Alpha-Fetoprotein L3 Fraction (AFP-L3) Using Blocked Labeled Lectin and Labeled Lectin (1) Preparation of Hydrazinated Dextran First, 240.0 mg of dextran (manufactured by CarboMer) having a molecular weight of 250 K was added to 4.8 mL of 0.1 M phosphate buffer (pH 7.0), and was dissolved by stirring in a dark place at 25° C. for 30 minutes. Subsequently, 2.664 mL of 150 mm NaIO$_4$ and 0.536 mL of ion-exchanged water were added thereto and the mixture was stirred in a dark place at 25° C. for 30 minutes. Using a. PD-10 column (manufactured by GE Healthcare, a Sephadex G-25 packed column), buffer exchange was performed with 0.1 M sodium phosphate buffer (pH 6.0) to obtain 20.0 mL of solution. Then, a of NH$_2$NH$_2$·HCl was added and the mixture was stirred in a dark place at 25° C. for 2 hours. Then, 800 mg of DMAB (dimethylamine borane) was added and the mixture was further stirred in a dark place at 25° C. for hours Dialysis using an RC50K (regenerated cellulose having a molecular weight of 50,000) membrane was performed with 4 L of ion-exchanged water in a dark place for 3 hours, followed by standing at 4° C. overnight. Buffer exchange was performed by gel filtration. (Sephadex G-25) using 0.1 M sodium phosphate buffer (pH 6.0) to obtain 85.0 mL of solution. The concentration of dextran was adjusted to 1.0 mg/mL, and a solution of hydrazinated dextran was obtained.

(2) Preparation of Dextran-Enzyme Conjugate 30.0 mL of 10 mg/mL alkaline phosphatase (manufactured by Oriental Yeast Co., Ltd., ALP-50) was subjected to buffer exchange by gel filtration (Sephadex G-25) using 0.1 M sodium phosphate buffer (pH 6.0) to prepare 90.6 mL of 3.0 mg/mL solution. Then, 45.3 mL of 27 mM NaIO$_4$ was added and the mixture was stirred in a dark place at 25° C. for 3 minutes. Buffer exchange was performed by gel filtration (Sephadex G-25) using 0.1 M sodium phosphate buffer (pH 6.0) to obtain 85.0 mL of solution. The 1.0 mg/mL hydrazinated dextran prepared in (1) of Reference Example 1 was added such that the concentration of the hydrazide group (amino group) became 25 μM, and the mixture was stirred in a dark place at 25° C. for 16 hours. Then, 85 mg of DMAB was added and the mixture was stirred in a dark place at 25° C. for 2 hours. Subsequently, 10.1 mL of 1.5 M Tris buffer (pH 9.0) was added and the mixture was stirred in a dark place at 25° C. for 2 hours. A ultrafiltration module (Pellicon XL50, manufactured by Merck Millipore) was attached to the Labscale TFF System (manufactured by Merck Millipore) to concentrate the mixture to 15 mL, and gel filtration (Superdex 200 pg) using 0.1 M sodium phosphate buffer (pH 7.0) was carried out to obtain 14 mL of solution of 3.0 mg/mL dextran-enzyme conjugate.

(3) Maleimide-PEGylation of Dextran-Enzyme Conjugate 0.1 M sodium phosphate buffer (pH 7.0) was added to the dextran-enzyme conjugate prepared in (2) of Reference Example 1 to prepare 750 μL of 2 mg/mL dextran-enzyme conjugate. To this, 8.35 μL of 250 mM SM(PEG)$_4$ (manufactured by Thermo Fisher Scientific, SM(PEG)$_4$) dissolved in DMSO was added and mixed, and the mixture was inverted and mixed in a dark place at 25° C. for 1 hour. After the reaction, buffer exchange using a. PD-10 column (Sephadex G-25) was performed to 0.1 M sodium phosphate buffer (pH 6.3) containing 20 mM EDTA·2Na and 0.5% CHAPS. After the buffer example, the maleimide-PEGylated dextran-enzyme conjugate was concentrated using a centrifugal filter (manufactured by Merck, Amicon Ultra 50K) to adjust the final concentration to 2 mg/mL.

(4) Thiolation of Lectin

First, 5 mg of *Lens culinaris* agglutinin (LCA; manufactured by J-CHEMICAL, Inc.) was dissolved in 2.5 mL of 0.1 M sodium phosphate buffer (pH 7.0) to obtain 2 mg/mL LCA solution. To 2.5 mL of the LAG solution, 100 μL of 0.5 M EDTA·2Na (pH 8.0) was added and mixed, and then 75 μL of 10 mg/mL 2-iminothiolane hydrochloride solution was added, followed by mixing with inversion in a dark place at 25° C. for 1 hour. After the reaction, buffer exchange using a PD-10 column (Sephadex G-25) was performed to 0.1 M sodium phosphate buffer (pH 6.3) containing 20 mM EDTA·2Na and 0.5% CHAPS. The LCA after the buffer exchange was adjusted to 650 μg/mL.

(5) Coupling

To 2 mL of the LCA tis elated and adjusted to 650 μg mL, which was obtained in (4) of Reference Example 1, 10 μL of 1 M glucose was added, and the mixture was inverted and mixed in a dark place at 25° C. for 30 minutes. Next, 500 μL of the solution of the maleimide-PEGylated dextran-enzyme conjugate (2 mg/mL) obtained in (3) of Reference Example 1 was added and the mixture was inverted and mixed in a dark place at 25° C. for 1 hour, so that the LCA and the dextran-enzyme conjugate were coupled. After the reaction, 25 μL of 200 mM 3-mercapto-1,2-propanediol was added, and the mixture was inverted and mixed in a dark place at 25° C. for 30 minutes. After that, 50 μL of 200 mM 2-iodoacetamide was further added, and the mixture was inverted and mixed in a dark place at 25° C. for 30 minutes. The solution after the reaction was concentrated using a centrifugal filter (manufactured by Merck, Amicon Ultra 50K), thereafter passed through a φ0.22 μm filter, and purified by gel filtration chromatography (column: Superose 6 Increase 10/300 GL, buffer: 0.1 M MES, 0.5 N NaCl, 1 mM MgCl$_2$, 0.1 mM ZnCl$_2$, 5 mM Glucose, 0.05% CHAPS, pH 6.8), so that 2 mL, of solution of 167.4 μg/mL blocked labeled lectin 1 (dextran-enzyme-LCA conjugate) was finally obtained.

(6) Preparation of Labeled Lectin

First, 5 mg of *Lens culinaris* agglutinin (LCA; manufactured by J-CHEMICAL, Inc.) was dissolved in 1 ml of 0.1 M sodium phosphate buffer (pH 7.0) to obtain 5 mg/mL LCA solution, To 1 mL Of the LAC solution, 41 μL of 10 mg/mL Sulfo-EMCS (manufactured by DOJINDO LABORATORIES) was added, and the mixture was inverted and mixed in a dark place at 25° C. for 1 hour. After the reaction, buffer exchange using a NAP-10 column (manufactured by GE Healthcare, a. Sephadex G-25 packed column) was performed to 0.1 M sodium phosphate buffer (pH 6.3) containing 0.5% CHAPS, and the recovered maleimidated LCA was adjusted to a concentration of 2.5 mg/mL.

300 μL of 10 mg/mL alkaline (manufactured by Oriental Yeast Co., Ltd., ALP-50) was subjected to buffer exchange using a NAP-5 column (manufactured by GE Healthcare, a Sephadex G-25 packed column) with 0.1 M sodium phosphate buffer (pH 7.0) to obtain 0.8 mL of 3.4 mg/mL ALP solution. Next, 13.2 μL of 10 mg/mL 2-iminothiolane hydrochloride solution was added, followed by mixing with inversion in a dark place at 25'C for 1 hour. After the rea buffer exchange using a NAP-10 column (Sephadex G-25) was performed to 0.1 M sodium phosphate buffer (pH 6.0) containing 0.5% CHAPS, and the recovered thiolated ALP was adjusted to a concentration of 1.8 mg/mL.

Then, 1.07 mL of the 2.5 mg/mL maleimidated LCA and 0.83 mL of the 1.8 mg/mL thiolated ALP were mixed and allowed to stand in a dark place at 25° C. for 20 hours to couple the LCA and the ALP. After the reaction, 19 μL of 150 mM 3-mercapto-1,2-propanediol was added and the mixture was allowed to stand in a dark place at 25° C. for 1 hour. The solution after the reaction was concentrated using a centrifugal filter (manufactured by Merck, Amicon Ultra 50K), thereafter passed through a φ0.22 μm filter, and purified by gel filtration chromatography (column: Superdex 200 PG, buffer: 0.1 M MES, 0.15 M NaCl, 1 mM MgCl$_2$, 1 mM ZnCl$_2$, 0.3 M Methyl-α-D-mannopyranoside, 0.05%

CHAPS, 0.9% NaN$_3$, pH 6.8), so that 1 ml of solution of 543 µg/mL labeled lectin 1 (ALP-LCA conjugate) was finally obtained.

(7) Measurement of AFP-L3

Magnetic particles (manufactured by FUJIREBIO Inc.) and anti-AFP monoclonal antibody F(ab')$_2$ fragments (manufactured by FUJIREBIO Inc.) were reacted to immobilize the antibody fragments on the particles. The particles on which the antibody fragments were immobilized were alkaline phosphatase of the blocked labeled lectin 1 or the labeled lectin 1 bound to the magnetic particles was measured. The measurement results were each output by an emission intensity (count) of the substrate. The measurement results under the respective conditions are shown in Table 1 presented below. Note that each of the presented results indicates a value obtained by subtracting a blank value obtained by measuring only the buffer from the average value in dual measurement

TABLE 1

| Label | Ref. Ex. 1-1 | Ref. Ex. 1-2 | Ref. Ex. 1-3 | Ref. Ex. 1-4 | Ref. Ex. 1-5 | Ref. Ex. 1-6 | Ref. Ex. 1-7 | Ref. Ex. 1-8 |
|---|---|---|---|---|---|---|---|---|
| | Blocked Labeled Lectin 1 | | | | Labeled Lectin 1 | | | |
| Free Dextran Concentration [%] | 0 | 1.0 | 2.0 | 3.0 | 0 | 1.0 | 2.0 | 3.0 |
| L3 Antigen 200 ng/mL | 335837 | 778428 | 1269328 | 1539225 | 20191 | 25949 | 37149 | 50376 |
| L1 Antigen 200 ng/mL | 0 | 0 | 0 | 0 | 0 | 0 | 0 | 0 | diluted at a particle concentration of 0.01% with a particle diluent (50 mM Tris, 100 mM KCl, 0.5% BSA, pH 7.2) to prepare a solution of anti-AFP antibody F(ab')$_2$ fragment-binding particles.

As a sample, a cancer-mutated AFP antigen (Huh7 cell culture serum-free supernatant, an AFP-L3 rate of 93. %, hereinafter also referred to as "L3 antigen") was diluted with Carbo-Free Blocking Solution (CFB; manufactured by VECTOR) at 200 ng/mL to prepare an L3 antigen analyte solution. In addition, a healthy person AFP antigen (manufactured by Lee Biosolutions, an AFP-L3 content rate of 7.8%, hereinafter also referred to as "L1 antigen") was diluted at 200 ng/mL with CFB to prepare an L1 antigen analyte solution as a reference sample.

Each of the blocked labeled lectin 1 obtained in of Reference Example 1 and the labeled lectin 1 obtained in (6) of Reference Example 1 was diluted at 0.5 µg/mL with a label diluent (30 mM MES, 360 mM NaCl, 1.5% arginine, 0.06% hydrazine hydrochloride, 0.06 mM ZnCl$_2$, 0.6 mM MgCl$_2$, 30 µg/mL inactivated ALP, 30 mL Mouse KLG, 2.4% C14APS, 0.15% Tween 20, 1×CFB, 1% Tergitol 15-s-7, 0.0005% Antiform SI), thereby preparing label solutions of the blocked labeled lectin 1 solution and the labeled lectin 1 solution. To each of the label solutions, free dextran 2000K (manufactured by Sigma) was added at 0%, 1.0%, 2.0%, or 3.0%.

AFP-L3 was measured using Lumipulse (registered trademark) L-2400 (manufactured by FUJIREBIO Inc.) for the above-mentioned L1 antigen analyte solution and L3 antigen analyte solution. Here, 50 µL of each of the analyte solutions and 50 µL of the aforementioned solution of anti-AFP antibody F(ab')$_2$ fragment-binding particles were mixed and reacted at 37° C. for 8 minutes. Next, the magnetic particles were collected and washed five times with a Lumipulse (registered trademark) washing liquid (manufactured by FUJIREBIO Inc.). Subsequently, 50 µL of each of the aforementioned label solutions was added, followed by reaction at 37° C. for minutes. Next, after the magnetic particles were collected and washed five times, 50 µL of a Lumipulse (registered trademark) substrate solution containing AMPPD (3-(2'-spiroadamantane)-4-methoxy-4-(3'-phosphoryloxy)phenyl-1,2-dioxetane-2-sodium salt) (manufactured by FUJIREBIO Inc.) was added, followed by reaction at 37° C. for 4 minutes. The amount of light with maximum absorption at a wavelength of 463 nm emitted by the decomposition of AMPPD by the catalytic action of the As shown in Table 1, it is observed that both of the blocked labeled lectin 1 and the labeled lectin 1 hardly bind to the L1 antigen but bind to the L3 antigen. In particular, in the case of using the blocked labeled lectin (Reference Examples 1-1 to 1-4), the signals obtained are higher than in the case of using the labeled lectin 1 (Reference Examples 1-5 to 1-8), which suggests that measurement with higher sensitivity is possible. Moreover, it is observed that, in the case where the free dextran is added to each of the label solutions, the signals obtained by using the blocked labeled lectin 1 achieve the significantly high values as compared with the labeled lectin 1.

Reference Example 2

Measurement of Prostate Cancer Cell-Derived PSA Using Blocked Labeled Lectin and Labeled Lectin 1
(1) Preparation of Blocked Labeled Lectin Using AAL 20 ml of solution of 87.6 µg/mL blocked labeled lectin 2 (dextran-enzyme-AAL conjugate) was obtained in the same manner as in (1) to (5) of Reference Example 1 except that *Aleuria aurantia* lectin AAL; manufactured by VECTOR) was used instead of the *Lens culinaris* agglutinin (LCA).
(2) Preparation of Labeled Lectin Using AAL 20 ml of solution of 34.4 µg/mL labeled lectin 2 (ALP-AAL conjugate) was obtained in the same manner as in (6) of Reference Example 1 except that the *Aleuria aurantia* lectin (AAL; manufactured by VECTOR) was used instead of the *Lens culinaris* agglutinin (LCA).
(3) Measurement of Cancer Cell-Derived PSA Magnetic particles (manufactured by FUJIREBIO Inc) and anti-PSA monoclonal antibody F(ab')$_2$ fragments (manufactured by FUJIREBIO Inc.) were reacted to immobilize the antibody fragments on the particles. The particles on which the antibody fragments were immobilized were diluted at a particle concentration of 0.01% with a particle diluent (50 mM Tris, 100 mM KCl, 0.5% BSA, pH 7.2) to prepare a solution of anti-PSA antibody F(ab')$_2$ fragment-binding particles.

Any of the blocked labeled lectin 2 (dextran-enzyme-AAL conjugate) obtained in (1) of Reference Example 2 and the labeled lectin 2 (ALP-AAL conjugate) obtained in (2) of Reference Example 2 was added at 0.5 µg/mL to PBS (pH 7.4) containing 1.0% BSA, 2.0% free dextran 2000K, and 0.0005% Antiform SI, thereby preparing each of the label solutions of the blocked labeled lectin 2 and the labeled lectin 2. As a sample, cultured prostate cancer cell (LNCaP)-derived PSA (LNCap-PSA) was diluted with CFB to prepare an analyte solution having a concentration of LNCap-PSA of 50 ng/mL.

The cancer cell-derived PSA was measured in the same manner as in (7) of Reference Example 1 except that the label solutions, the analyte solution, and the solution of anti-PSA antibody F(ab')$_2$ fragment-binding particles described above were used. The measurement results of the cancer cell-derived PSA under the respective conditions (an emission intensity (count) of the substrate) are shown in Table 2 presented below. Note that each of the presented results indicates a value obtained by subtracting a blank value obtained by measuring only the buffer from the average value in dual measurement.

TABLE 2

| Label | Ref. Ex. 2-1 Block Labeled Lectin 2 | Ref. Ex. 2-2 Labeled Lectin 2 |
|---|---|---|
| LNCap-PSA [50 ng/mL] | 15319176 | 628466 |

Table 2 indicates that both of the blocked labeled lectin 2 and the labeled leetin 2 are capable of detecting the cancer cell-derived PSA. In particular, in the case of using the blocked labeled lectin 2 (Reference Example 2-1), the signal obtained is higher than in the case of using the labeled lectin 2 (Reference Example 2-1), which suggests that measurement with higher sensitivity is possible.

Example 1

Purification Treatment of Sample in AFP-L3 Measurement in Serum

As samples, CFB containing 200 ng/mL L3 antigen (B1, buffer analyte), healthy person serum to which L3 antigen was added at 200 ng/mL (S1, serum analyte), and healthy person serum to which no L3 antigen was added (52, serum analyte) were prepared.
(1) Sample Purification Treatment 40 μL of anti-AFP antibody-binding particles (manufactured by FUJIREBIO Inc.) and 300 μL of each of the serum analytes (51 or 52) were mixed, and the mixture was stirred and shaken at room temperature for 40 seconds. After the magnetic particles were collected and supernatant was removed, magnetic particles were washed three times with 300 μL of a Lumipulse (registered trademark) washing liquid. Then, 200 μL of an eluate (0.1 M Glycine, 0.3 M NaCl, 0.2% Triton X-100, 1×CFB, pH 2.1) was added, and the mixture was stirred and shaken at room temperature for 20 seconds. The supernatant was transferred to another container and neutralized by adding 10 μL of a neutralizer (2M Tris, pH 10.0), and then 90 μL of CFB was added to prepare each purified sample.
(2) Measurement of AFP-L3

Each of the blocked labeled lectin 1 obtained in (5) Reference Example 1 and the labeled lectin 1 obtained in (6) of Reference Example 1 was diluted at 0.5 μg/mL with a label diluent (30 mM MES, 360 mM NaCl, 1.5% arginine, 0.06 mM ZnCl$_2$, 0.6 mM MgCl$_2$, 30 μg/mL Inactivated ALP, 30 μg/mL Mouse. KLG, 2.4% C14APS, 0.15% Tween 20, 1×CFB, 1% Tergitol 15-s-7, 2% free dextran 2000K, 0.0005% Antiform SI), thereby preparing each of the label solutions of the blocked labeled lectin 1 solution and the labeled lectin 1 solution.

AFP-L3 in 51 and S2 purified by the purification treatment in (1) of Example 1 was measured in the same manner as in (7) of Reference Example 1 except that the label solutions described above were used (Example 1-1). In addition, AFP-L3 in S1, S2, and B1 was measured under the condition where the purification treatment in (1) of Example 1 was not performed and the other conditions set to the same as the above (Comparative Example 1-1). The measurement results of AFP-L3 under the respective conditions (an emission intensity (count) of the substrate) are shown in Table 3 presented below. Note that each of the presented results indicates a value obtained by subtracting a blank value obtained by measuring only the buffer from the average value in dual measurement.

TABLE 3

| | Purification Treatment | Sample | Blocked Labeled Lectin 1 | Labeled Lectin 1 |
|---|---|---|---|---|
| Comp. Ex 1-1 | Not Purified | B1 | 558150 | 63707 |
| | | S1 | 797593 | 438732 |
| | | S2 | 489568 | 382116 |
| Ex. 1-1 | Purified | S1 | 526653 | 131836 |
| | | S2 | 21680 | 12556 |

As shown in Table 3, a high signal was detected in the healthy person serum analyte (S2) in the case where the purification treatment was not performed. (Comparative Example 1-1), As a result of the purification treatment (Example 1-1), the signal from the serum analyte (S1) containing a larger amount of AFP-L3 was also decreased, but the signal from the healthy person serum analyte (S2) was remarkably decreased as compared with the case where the purification treatment was not performed (Comparative Example 1-1), which confirms that it is possible to measure AFP-L3 with high accuracy in particular.

Example 2

Purification Treatment of Sample in Measurement of Prostate Cancer Cell-Derived PSA in Serum As samples, CFB containing 50 ng/mL LNCap-PSA (B2, buffer analyte), healthy person serum to which LNCap-PSA was added at 50 ng/mL (S3, serum analyte), and healthy person serum to which no LNCap-PSA was added (S4, serum analyte) were prepared,
(1) Sample Purification Treatment 40 μL of anti-PSA antibody-binding particles (manufactured by FUJIREBIO Inc.) and 300 μL of each of the serum analytes (S3 or S4) were mixed, and the mixture was stirred and shaken at room temperature for 40 seconds. After the magnetic particles were collected and the supernatant was removed, the magnetic particles were washed three times with 300 μL of a Lumipulse (registered trademark) washing liquid. Then, 200 μL of an eluate (0.1 M Glycine, 0.15 M NaCl, 1×CFB, pH 1.0) was added, and the mixture was stirred and shaken at room temperature for 20 seconds. The supernatant was transferred to another container and neutralized by adding 20 μL of 2 M Tris (pH 10.0), and then 80 μL of CFB was added to prepare each purified sample.
(2) Measurement of Cancer Cell-Derived PSA The blocked labeled lectin 2 obtained in (1) of Reference Example 2 or the labeled lectin 2 obtained in (1) of Reference Example 2 was diluted at 0.5 μg/mL with a label diluent (PBS containing 1.0% BSA, 2.0% free dextran 2000K, and 0.0005% Antiform SI, pH 7.4), thereby preparing each of the label solutions of the blocked labeled lectin 2 solution and the labeled lectin 2 solution.

The cancer cell-derived PSA in 53 and 54 purified by the purification treatment in (1) of Example 2 was measured in the same manner as in (3) of Reference Example 2 except that the label solutions described above were used (Example 2-1). In addition, the cancer cell-derived PSA in S3, S4, and B3 was measured under the condition where the purification treatment in (1) of Example 2 was not performed and the other conditions set to the same as the above (Comparative Example 1). The measurement results of the cancer cell-derived PSA under the respective conditions (an emission intensity (count) of the substrate) are shorn in Table 4 presented below. Note that each of the presented results indicates a value obtained by subtracting a blank value obtained by measuring only the buffer from the average value in dual measurement.

TABLE 4

|  | Purification Treatment | Sample | Blocked Labeled Lectin 2 | Labeled Lectin 2 |
|---|---|---|---|---|
| Comp. Ex 2-1 | Not Purified | B2 | 15319176 | 628466 |
|  |  | S3 | 16292895 | 949203 |
|  |  | S4 | 3908490 | 190141 |
| Ex. 2-1 | Purified | S3 | 3955129 | 203800 |
|  |  | S4 | 1205083 | 80390 |

As shown in Table 4, a high signal was detected in the healthy person serum analyte (S3) in the case where the purification treatment was not performed (Comparative Example 2-1), As a result of the purification treatment (Example 2-1), the signal from the serum al analyte (S3) containing the cancer cell-derived PSA was also decreased, but the signal from the healthy person serum analyte (54) was remarkably decreased as compared with the case where the purification treatment was not performed (Comparative Example 2-1), which confirms that it is possible to measure the cancer cell-derived PSA with high accuracy in particular.

Example 3

Using AFP as an example, whether a measurement target substance can be concentrated was examined by changing the volume of an eluate in the purification treatment using the capture carrier (antibody-binding particles). Specifically, first, as a sample prior to the purification treatment, healthy person serum to which L3 antigen was added at 200 ng/mL (primary analyte) was prepared. Next, 300 μL of the sample prior to the purification treatment was purified by the purification treatment in the same manner as in (1) of Example 1 except that the following conditions were set as an elution condition, so that prepared samples were obtained. The elution condition was a condition where the volume of an eluate and a neutralizer for particles, which were obtained after being mixed with each sample, collected followed by supernatant removal, and then washed, was changed such that the prepared sample obtained had a liquid volume (final liquid volume) of 300 μL, 200 μL, 150 μL, or 100 μL.

AFP and AFP-L3 in each of the prepared samples after the purification treatment were measured by tests on the Lumipulse Presto (registered trademark) II (manufactured by FUJIREBIO Inc.) using an AFP measurement reagent (manufactured by FUJIREBIO Inc.) and the blocked labeled lectin 1 obtained in (5) of Reference Example 1, The measurement of AFP-L3 by using the blocked Labeled lectin 1 was conducted under the same conditions ae in (7) of Reference Example 1, and the concentration of free dextran added to the label solution was set to 1 The measurement result in the liquid volume of each of the prepared samples is shown in Table 5 presented below. Note that each of the presented results indicates the average value in dual measurement.

TABLE 5

| Pre Purification | Post-Purification Treatment | | |
|---|---|---|---|
| Treatment Liquid Volume | Liquid Volume | APF Measurement Reagent | Blocked Labeld Lectin 1 |
| 300 μL | 300 μL | 1068564 | 378631 |
|  | 200 μL | 1681947 | 510102 |
|  | 150 μL | 1990644 | 588688 |
|  | 100 μL | 2907922 | 691564 |

As shown in Table 5, both of the measurement count of AFP (the AFP measurement reagent) and the measurement count of AFP-L3 (the blocked labeled lectin 1) in the prepared samples were increased along with a reduction in the volume of the eluate and the neutralizer, which indicates the increases in the concentrations of AFP and AFP-L3. These results confirm that the lectin-binding substance can be concentrated when a smaller liquid volume of the prepared sample than the liquid volume of the sample prior to the purification treatment is obtained by changing the elution condition of the lectin-binding substance in the process of the sample purification treatment.

INDUSTRIAL APPLICABILITY

According to the present invention, it is possible to provide a lectin-binding substance measurement method and a lectin-binding substance measurement kit which are capable of measuring a lectin-binding substance in a sample with high sensitivity in a simple procedure, and provide a capture carrier for use in these.

The invention claimed is:

1. A lectin-binding substance measurement method for measuring a lectin-binding substance in a sample, the method comprising:
  purifying the lectin-binding substance by steps including at least
    a capturing step of bringing a capture carrier including a water-insoluble carrier and a molecule immobilized on the water-insoluble carrier, the molecule being a molecule capable of capturing a lectin-binding substance, into contact with the sample to cause the capture carrier to capture the lectin-binding substance;
    a washing step of removing contaminants unbound to the capture carrier; and
    a releasing step of releasing the lectin-binding substance from the capture carrier to obtain a prepared sample; and
  measuring the purified lectin-binding substance in the prepared sample by using a lectin, wherein
    the lectin is at least one of
      a labeled lectin including a labeling substance and a lectin, and a blocked labeled lectin including a water-soluble carrier made of a first water-soluble polymer, a labeling substance and a lectin immobilized on the water-soluble carrier, the lectin-binding substance is a substance having a glycan capable of binding to a lectin, the molecule capable of capturing the lectin-binding substance is a molecule capable of recognizing and binding to a portion other than the glycan portion in the lectin-binding substance, and the capture carrier does not include the labeling substance.

2. The lectin-binding substance measurement method according to claim 1, wherein the measuring includes a step of bringing the labeled lectin into contact with the prepared sample.

3. The lectin-binding substance measurement method according to claim 1, wherein the measuring includes a step of bringing the blocked labeled lectin into contact with the prepared sample.

4. The lectin-binding substance measurement method according to claim 1, wherein the measuring is carried out in the presence of a free second-water-soluble polymer.

* * * * *